(12) United States Patent
Bhullar et al.

(10) Patent No.: US 6,447,657 B1
(45) Date of Patent: Sep. 10, 2002

(54) BIOSENSOR

(75) Inventors: Raghbir S. Bhullar, Indianapolis; Christopher D. Wilsey, Carmel; Brian S. Hill, Avon, all of IN (US)

(73) Assignee: Roche Diagnostics Corporation, Indianapolis, TN (US)

( * ) Notice: Subject to any disclaimer, the term of this patent is extended or adjusted under 35 U.S.C. 154(b) by 0 days.

(21) Appl. No.: 09/729,296

(22) Filed: Dec. 4, 2000

(51) Int. Cl.[7] ............................................. G01N 27/26
(52) U.S. Cl. ..................... 204/409; 204/403; 204/416
(58) Field of Search .............................. 204/403, 416, 204/409

(56) References Cited

U.S. PATENT DOCUMENTS

| 4,963,814 A | 10/1990 | Parks et al. ................. 323/274 |
| 4,999,582 A | 3/1991 | Parks et al. ................. 324/438 |
| 4,999,632 A | 3/1991 | Parks ........................ 341/167 |
| 5,120,420 A | 6/1992 | Nankai et al. .............. 204/403 |
| 5,141,868 A | 8/1992 | Shanks et al. .............. 435/288 |
| 5,243,516 A | 9/1993 | White ................... 364/413.07 |
| 5,264,103 A | 11/1993 | Yoshioka et al. ........... 204/403 |
| 5,320,732 A | 6/1994 | Nankai et al. .............. 204/403 |
| 5,352,351 A | 10/1994 | White et al. ................ 204/406 |
| 5,366,609 A | 11/1994 | White et al. ................ 204/403 |
| 5,405,511 A | 4/1995 | White et al. ............. 204/153.1 |
| 5,437,999 A | 8/1995 | Diebold et al. ............. 435/288 |
| 6,156,173 A | * 12/2000 | Gotoh et al. ................ 204/403 |
| 6,299,757 B1 | * 10/2001 | Feldman et al. ............ 205/775 |

FOREIGN PATENT DOCUMENTS

| EP | 0 851 224 | 7/1998 |
| EP | 0 964 059 | 12/1999 |
| JP | 11 125618 | 5/1999 |
| WO | WO 99/18439 | 4/1999 |
| WO | WO 00/73778 | 12/2000 |
| WO | WO 00/73785 | 12/2000 |

* cited by examiner

Primary Examiner—T. Tung
Assistant Examiner—Alex Noguerola
(74) Attorney, Agent, or Firm—Jill Woodburn (57) ABSTRACT

A biosensor is provided that includes first and second plate elements, wherein each plate elements has first and second ends and first and second lateral borders. In addition, the biosensor includes a spacer positioned to lie between the first and second plate elements so that at least a portion of the first and second plate elements cooperate with one another to form opposite walls of a capillary space. Further, the first ends and at least a portion of the lateral borders define a fluid sample-receiving portion in communication with the capillary space. Electrodes are positioned in the capillary space of the biosensor.

29 Claims, 4 Drawing Sheets

BIOSENSOR

FIELD OF THE INVENTION

The present invention relates to a biosensor and particularly to an electrochemical biosensor.

BACKGROUND AND SUMMARY OF THE INVENTION

Electrochemical biosensors are known. They have been used to determine the concentration of various analytes from biological samples, particularly from blood. Biosensors are described in U.S. Pat. Nos. 5,413,690; 5,762,770; 5,798,031; and 5,997,817, the disclosure of each of which are expressly incorporated herein by reference.

According to the present invention a biosensor is provided. The biosensor comprises first and second plate elements, said plate elements having first and second ends and first and second lateral borders, a spacer positioned to lie between the first and second plate elements so that at least a portion of the first and second plate elements cooperate is with one another to form opposite walls of a capillary space and the first ends and at least a portion of the lateral borders define a fluid sample receiving portion in communication with the capillary space, and electrodes positioned in the capillary space.

In addition, a biosensor is provided that comprises first and second plate elements, said plate elements having tabs with ends and first and second lateral borders, electrodes positioned on the tab of said first plate element, and a spacer positioned to lie between the plate elements so that the tabs form opposite walls of a capillary space extending between lateral borders and ends, wherein the ends and lateral borders cooperate to define a fluid sample receiving portion in communication with the capillary space.

Additional features of the invention will become apparent to those skilled in the art upon consideration of the following detailed description of the preferred embodiment exemplifying the best mode of carrying out the invention.

BRIEF DESCRIPTION OF THE DRAWINGS

The detailed description particularly refers to the accompanying figures in which.

DETAILED DESCRIPTION OF THE DRAWINGS

Figure 1:
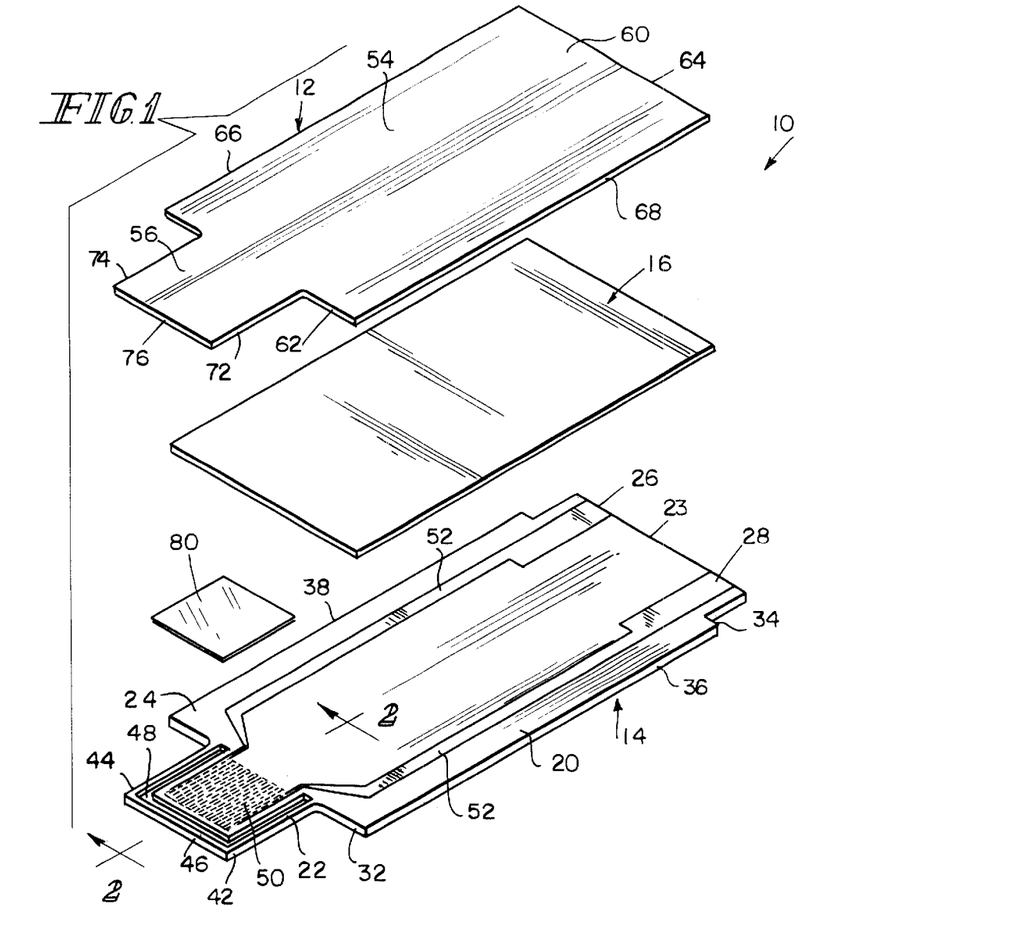
FIG. 1 is an exploded perspective view of a biosensor in accordance with the present invention.
Figure 2:
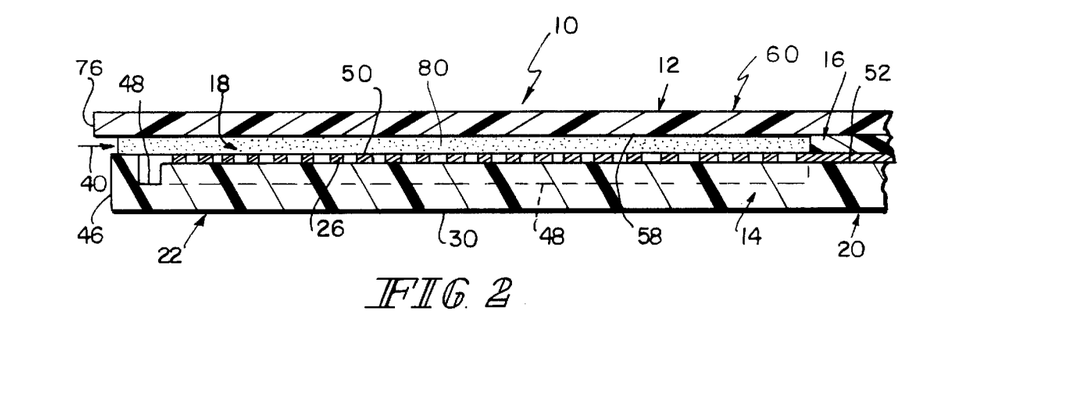
FIG. 2 is an assembled sectional view taken along lines 2—2 of FIG. 1.

A biosensor 10 in accordance with the present invention is shown in FIG. 1, as it would appear to a user just prior to use. As shown in FIG. 2, biosensor 10 compensates for small sample volumes by providing a cantilever based capillary design. Biosensor 10 is an economical disposable sensor with an integrated design, which can handle as low as about 500 nL sample volume.

FIGS. 1–11 illustrate an aspect of the invention in the form of biosensor 10 having a top plate element 12 and a bottom plate element 14, electrically conductive tracks 26, 28 and a reagent 80 situated between plate elements 12, 14, and a spacer 16. Spacer 16 separates top and bottom elements 12, 14, a portion of which cooperate with one another to define a cantilevered capillary channel 18. Biosensor 10 is preferably rectangular in shape. It is appreciated, however, that biosensor 10 can assume any number of shapes and can include more than one cantilevered capillary channel 18 in accordance with this disclosure. Biosensor 10 is preferably produced from rolls of material, however, it is understood that biosensor 10 can be constructed from individual sheets in accordance with this disclosure. Thus, when biosensor 10 is to produced from rolls of material, the selection of materials for the construction of biosensor 10 necessitates the use of materials that are sufficiently flexible for roll processing, but which are still rigid enough to give a useful stiffness to finished biosensor 10. Various aspects of the invention are presented in FIGS. 1–11, which are not drawn to scale and wherein like components in the several views are numbered alike.

Bottom plate element 14 of biosensor 10 includes a body portion 20, a tab 22, and a connection portion 23. The body portion 20, tab 22, and connection portion 23 each includes a first surface 24 that supports conductive tracks 26, 28 and an opposite second surface 30. See FIGS. 1 and 2. In addition, body portion 20 has opposite ends 32, 34 and edges 36, 38 extending between ends 32, 34. First end 32 from which tab 22 extends has a pre-determined width, which can vary in accordance with this disclosure. Connection portion 23 extends from opposite end 34 of body portion 20.

Tab 22, includes lateral borders 42, 44 and an end 46. Lateral borders 42, 44 have a pre-determined width that is less than the width of end 32 of body portion 20. In addition, tab 22 is formed to include a recess 48. Recess 48 is formed to have three sides and extend from end 32 and about electrodes 26, 28. A detailed description of recess 48 is found in U.S. patent application Ser. No. 09/704,145, entitled "BIOSENSOR", which was filed in the U.S. Patent and Trademark Office on Oct. 6, 2000, to Bhullar et al., the disclosure of which is expressly incorporated herein by reference. It is appreciated, that biosensor can be formed without recess 48 in accordance with this disclosure. Further, bottom element 14 may be constructed from a wide variety of insulative materials. Non-limiting examples of insulative materials that provide desirable electrical and structural properties include glass, ceramic, vinyl polymers, polyimides, polyesters, and styrenics. Preferably, bottom plate element 14 is a flexible polymer, such as a polyester or polyimide. A non-limiting example of a suitable material is 5 mil thick KALADEX® commercially available from E.I. DuPont de Nemours, Wilmington, Del.

Figure 3:
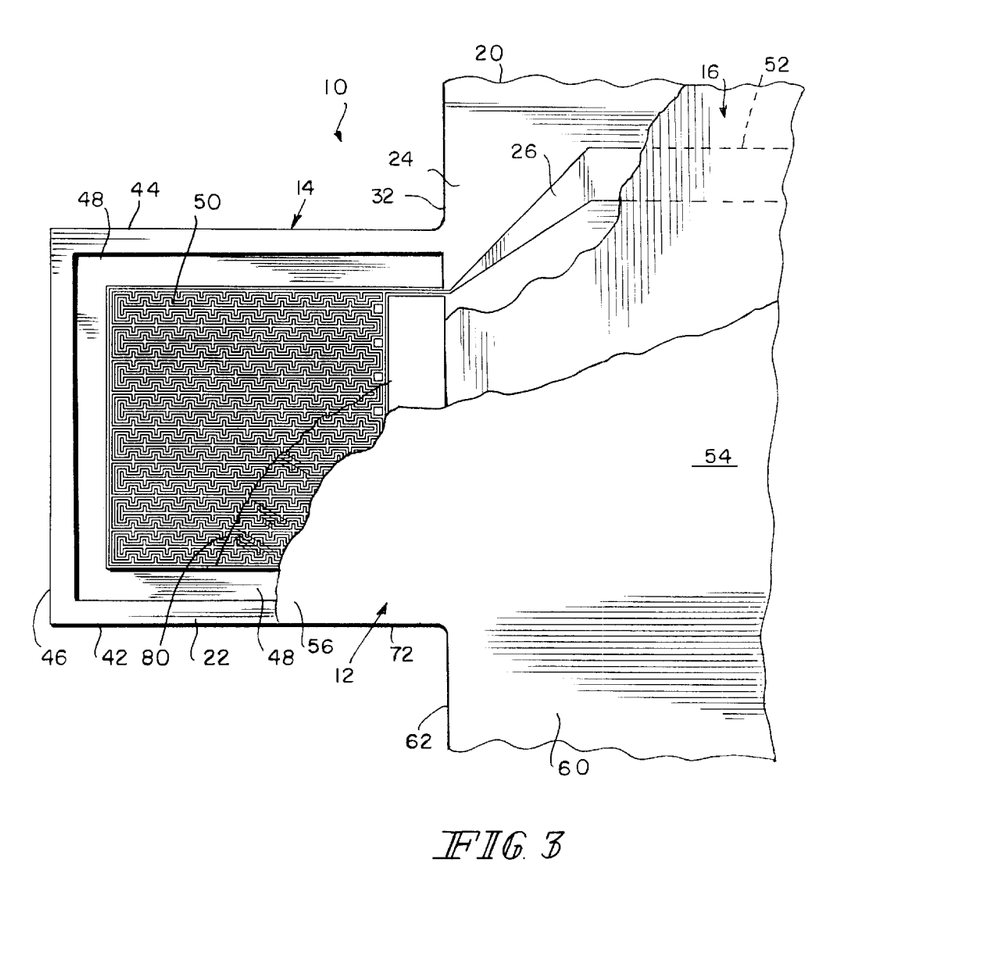
FIG. 3 is an enlarged top view, with portions broken away, of the biosensor of FIG. 1.

As shown in FIGS. 1 and 3, electrically conductive tracks 26, 28 are created or isolated on first surface 24 of plate element 14. Tracks 26, 28 represent the electrodes set of biosensor 10. As used herein, the phrase "electrode set" is a set of at least two electrodes, for example 2 to 200, or 3 to 20, electrodes. These electrode sets may, for example, include a working electrode and an auxiliary electrode. Tracks 26, 28 cooperate to form an interdigitated electrode array 50 positioned on tab 22 and leads 52 that extend from array 50 across body portion 20 to end 34. Track 26 may be a working electrode and track 28 may be an auxiliary electrode.

Tracks 26, 28 are constructed from electrically-conductive materials. Non-limiting examples of electrically-conductive materials include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, tracks include gold, platinum, palladium, iridium, or alloys of these metals, since such noble metals and their alloys are unreactive in biological systems. Most preferably, track 26 is a working electrode made of gold, and track 28 is an auxiliary electrode that is also made of gold and is substantially the same size as the working electrode.

Tracks 26, 28 are preferably isolated from the rest of the electrically conductive surface by laser ablation. Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE",the disclosure of which is expressly incorporated herein by reference. Tracks 26, 28 are preferably created by removing the electrically conductive material from an area extending around the electrodes. Therefore, tracks 26, 28 are isolated from the rest of the electrically-conductive material on bottom element 14 by a gap having a width of about 25 $\mu$m to about 500 $\mu$m, preferably the gap has a width of about 100 $\mu$m to about 200 $\mu$m. Alternatively, it is appreciated that tracks 26, 28 may be created by laser ablation alone on bottom element 14. Further, tracks 26, 28 may be laminated, screen-printed, or formed by photolithography in accordance with this disclosure.

Multi-electrode arrangements are also possible in accordance with this disclosure. For example, it is contemplated that a biosensor may be formed that that includes an additional electrically conductive track (not shown). In a three-electrode arrangement, the first track is a working electrode, the second is a counter electrode, and the third electrode is a reference electrode. It is also appreciated that an alternative three-electrode arrangement is possible where tracks are working electrodes and a third electrode is provided as an auxiliary or reference electrode in accordance with this disclosure. It is appreciated that the number of tracks, as well as the spacing between tracks in array 50 may vary in accordance with this disclosure and that a number of arrays may be formed as will be appreciated by one of skill in the art.

Reagent 80 provides electrochemical probes for specific analytes and is positioned in opening 18 such that reagent 80 covers interdigited electrode array 50. Reagent 80 is placed as a film of generally uniform thickness over first surface 24 of tab 22 and across array 50. Reagent 80 will then present a hydrophilic surface to the interior of capillary opening 18.

The choice of specific reagent 80 depends on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100–900 kilodaltons), 3.3 mg NATROSOL 250M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is incorporated herein by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight:volume) Avicel. A further description of the reagent for a hematocrit assay is found in U.S. Pat. No. 5,385,846, the disclosure of which is incorporated herein by reference.

Non-limiting examples of enzymes and mediators that may be used in measuring particular analytes in sensor 10 of the present invention are listed below in Table 1.

TABLE 1

| Analyte | Enzymes | Mediator (Oxidized Form) | Additional Mediator |
| --- | --- | --- | --- |
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |

TABLE 1-continued

| Analyte | Enzymes | Mediator (Oxidized Form) | Additional Mediator |
|---|---|---|---|
| HDL Cholesterol | Cholesterol Lsterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample may be accurately correlated to the concentration of the analyte in the sample with biosensor 10 in accordance with this disclosure.

Referring again to FIG. 1, spacer 16 of biosensor 10 is positioned to lie between top and bottom plate elements 12, 14. Moreover, spacer 16 cooperates with top and bottom plate elements 12, 14 to expose array 50 to a liquid sample being applied to biosensor 10 in capillary channel as shown by arrow 40 in FIG. 2. Spacer 16 is a double-coated adhesive tape that is coupled to bottom plate element 14 and tracks 16, 18. A non-limiting example of such an adhesive is 3M High Performance Double Coated Tape 9500 PC, commercially available from Minnesota Mining and Manufacturing Company, St. Paul, Minn. It is appreciated that spacer 16 may be constructed of a variety of materials and may be coupled to top and bottom plate elements 12, 14 using a wide variety of commercially available adhesives. Additionally, when surface 24 of element 14 is exposed and not covered by electrical conductor, spacer 16 may be coupled to plate element 14 by welding (heat or ultrasonic) in accordance with this disclosure.

Top plate element 12 of biosensor 10 includes a first surface 58 facing spacer 16 and an opposite second surface 60. See FIG. 2. Top plate element 12 of biosensor 10 includes a body portion 54 that overlaps tracks 26, 28 and a tab 56 extending from body portion 54 across array 50. In addition, body portion 54 has opposite ends 62, 64 and edges 66, 68 extending between ends 62, 64. First end 62 from which tab 56 extends has a pre-determined width. This width of end 62 is generally equal to the width of end 32, although it is appreciated that this width can vary in accordance with this disclosure.

Tab 56 of top plate element 12, includes lateral borders 72, 74 and an end 76. Lateral borders 72, 74 have a pre-determined width that is less than the width of end 62 of body portion 54. Upon assembly, end 64 of body portion 54 is positioned in general alignment with end 34 of body portion 20. It is appreciated that extent to which tracks 26, 28 are exposed for electrical connection with a meter (not shown), which measures some electrical property of a liquid sample after the sample is applied to biosensor 10. Top plate element 12 may be constructed from a wide variety of insulative materials. Non-limiting examples of insulative materials that provide desirable properties include glass, ceramics, vinyl polymers, polyimides, polyesters, and styrenics. Preferably, top plate element 12 is a flexible polymer, such as a polyester or polyimide. A non-limiting example of a suitable material is 7 mil thick MELINEX® 329 commercially available from E.I. DuPont de Nemours, Wilmington, Del.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in cassette magazine, or packed in a blister packaging.

Below is a non-limiting example of the use of biosensor 10 in conjunction with the following:
1. a power source in electrical connection with the electrodes and capable of supplying an electrical potential difference between the electrodes sufficient to cause diffusion-limited electro-oxidation of the reduced form of the mediator at the surface of the working electrode; and
2. a meter in electrical connection with the electrodes and capable of measuring the diffusion-limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby expressly incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, blood is assayed with this invention.

In use, the user places a liquid sample against tabs 22, 56 of biosensor 10. The liquid sample will be drawn into capillary channel as shown by arrow 40 in FIG. 2. When reagent 80 is the reagent for measuring glucose as discussed above, sample containing the analyte dissolves reagent 80 in capillary channel 18 to oxidize the analyte and reduce the oxidized form of the mediator. The reaction between the analyte and reagent 80 is permitted to go to completion. (Completion is defined as sufficient reaction involving analyte, enzyme, and mediator (oxidized form) to correlate analyte concentration to diffusion-limited current generated by oxidation of the reduced form of the mediator at the surface of the working electrode.)

After reaction is complete, a power source (e.g., a battery) applies a potential difference between electrodes. When the potential difference is applied, the amount of oxidized form of the mediator at the auxiliary electrode and the potential difference must be sufficient to cause diffusion-limited electro-oxidation of the reduced form of the mediator at the surface of the working electrode. A current measuring meter (not shown) measures the diffusion-limited current generated by the oxidation of the reduced form of the mediator at the surface of the working electrode. The measured current may be accurately correlated to the concentration of the analyte in sample when the following requirements are satisfied:

1. The rate of oxidation of the reduced form of the mediator is governed by the rate of diffusion of the reduced form of the mediator to the surface of the working electrode.
2. The current produced is limited by the oxidation of reduced form of the mediator at the surface of the working electrode.

To manufacture biosensor 10 a roll of metallized film is fed through guide rolls into an ablation/washing and drying station. A laser system capable of ablating bottom element material is known to those of ordinary skill in the art. Non-limiting examples of which include excimer lasers, with the pattern of ablation controlled by mirrors, lenses, and masks. A non-limiting example of such a system is the LPX-300 or LPX-200 both commercially available from LPKF Laser Electronic GmbH, of Garbsen, Germany.

In the laser ablator, the metallic layer of the metallized film is ablated in pre-determined patterns, to form a ribbon of isolated electrode sets. The metallized film is further ablated, after the isolated electrode sets are formed, to create recesses 48 positioned adjacent to each electrochemical area. The ribbon is then passed through more guide rolls, with a tension loop and through an optional optical or electrical inspection system. This inspection system(s) is used for quality control in order to check for defects.

Reagent 80 is compounded and applied in a liquid form to the center of array 50 at a dispensing and drying station. Reagent 80 can be applied bellowed dispenser commercially available from Fluilogic Systems Oy, Espoo, Findland. It is appreciated that reagent may be applied to array 50 in a liquid or other form and dried or semi-dried onto the center of array 50 in accordance with this disclosure.

In addition, a roll or top plate element material is fed into a punching station to punch out contours of tab 56 in top plate element material. Next, the top plate element material is fed into an assembly station along with a roll of spacer material. Liners on either side of the spacer material are. removed in that station and the top plate element is applied to one side of the spacer material to form a top plate element/spacer subassembly. The top plate element/spacer subassembly is slit into the appropriate width for a row of biosensors 10. Next, a new release liner is added to the side of the spacer material opposite the cover and the subassembly is wound into a roll. It is appreciated that any number of commercially available dispense units, cutting units, and sensor punch units may be used to form biosensor 10 in accordance with this disclosure.

The ribbon of the reagent-coated bottom plate element is unwound and fed into a sensor assembly station along with the top plate element/spacer subassembly. The liner is removed from the spacer and the subassembly is placed on bottom plate element 14 to cover reagent 80. Next, the assembled material is cut to form individual biosensors 10, which are sorted and packed into vials, each closed with a stopper containing desiccant, to give packaged sensor strips.

The processes and products described above include a disposable biosensor, especially for use in diagnostic devices. Also included, however, are electrochemical sensors for non-diagnostic uses, such as measuring an analyte in any biological, environmental, or other sample. As discussed above, biosensor 10 can be manufactured in a variety of shapes and sizes. Non-limiting examples of which are illustrated in FIGS. 4–13. Each of the biosensors illustrated in FIGS. 4–13 are formed similarly to biosensor 10, except for the shape of their tabs.

Figure 4:
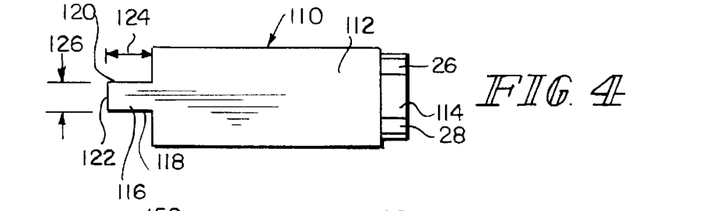
FIG. 4 is a top view of a biosensor in accordance with another embodiment of the invention.

Referring now to FIG. 4, biosensor 110 includes top and bottom plates 112, 114 separated by a spacer 115. Plates 112, 114 are each formed to include a rectangular-shaped tab 116. Tab 116 includes lateral borders 118, 120 and an end 122. Illustratively, borders 118, 120 are generally parallel relative to one another and have a first dimension 124 that is greater than the second dimension 126 of end 122. It is appreciated that the relative dimensions between first and second dimensions 124, 126 may vary in accordance with this disclosure so long as first dimension 124 is greater than second dimension 126.

Figure 5:
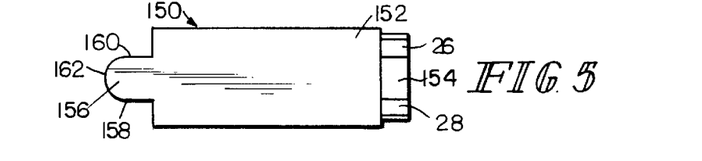
FIG. 5 is a top view of a biosensor in accordance with another embodiment of the invention.

As shown in FIG. 5, biosensor 150 includes top and bottom plates 152, 154 separated by a spacer 164. Plates 152, 154 are each formed to include a curved tab 156. Tab 156 includes curved lateral borders 158, 160 that meet at an end 162. It is appreciated that borders 158, 160 can be formed with a variety of degrees of curvature in accordance with this disclosure.

Figure 6:
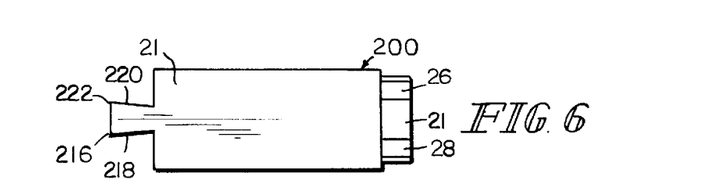
FIG. 6 is a top view of a biosensor in accordance with another embodiment of the invention.

Biosensor 200 is provided in accordance with another aspect of this invention and is illustrated in FIG. 6. Biosensor 200 includes top and bottom plates 212, 214 separated by a spacer 224. Plates 212, 214 are each formed to include a tab 216. Tab 216 includes lateral borders 218, 220 and an end 222. Illustratively, borders 218, 220 diverge toward end 222. It is appreciated that borders 218, 220 can be formed to have a variety of degrees of divergence relative to one another in accordance with this disclosure.

Figures 7, 8, 11:
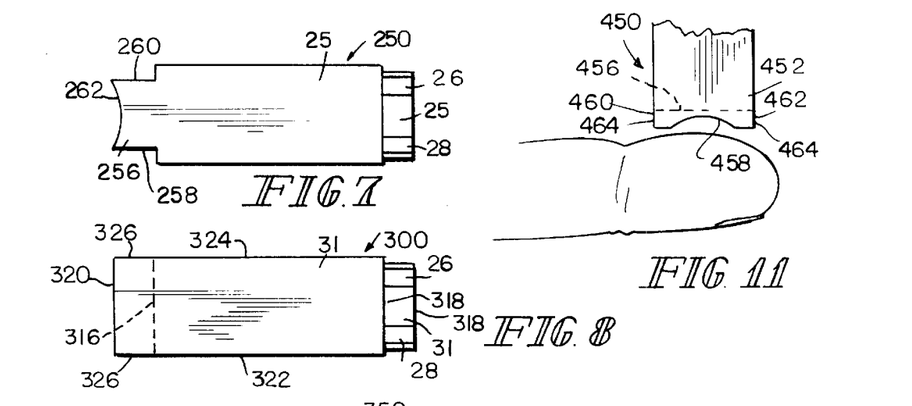
FIG. 7 is a top view of a biosensor in accordance with another embodiment of the to invention.
FIG. 8 is a top view of a biosensor in accordance with another embodiment of the invention.
FIG. 11 is a top view of a biosensor in accordance with another embodiment of the invention.

Biosensor 250 is shown in FIG. 7 and includes top and bottom plates 252, 254 separated by a spacer 264. Plates 252, 254 are each formed to include a tab 256. Tab 256 includes generally straight lateral borders 258, 260 and an end 262. Borders are positioned generally parallel relative to one another and end 262 is generally concave in shape. It is appreciated that end 262 with a variety of degrees of curvature, or may be indented in any number of manners in accordance with the disclosure.

Referring now to FIG. 8, biosensor 300 includes top and bottom plates 312, 314, which are separated from one another by a spacer 316. Each plate 312, 314 has opposite ends 318, 320 and opposite lateral borders 322, 324. Additionally, ends 320 and a portion 326 of lateral borders 322, 324 define a fluid sample-receiving portion in communication with the capillary space. It is appreciated that the length of portion 326 of lateral borders 322, 324 may vary in accordance with this disclosure.

Figure 9:
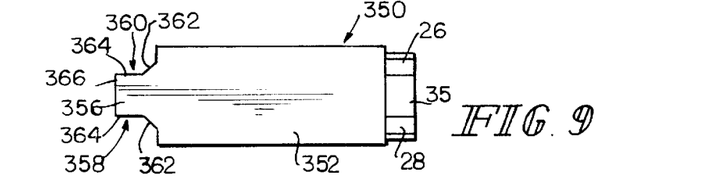
FIG. 9 is a top view of a biosensor in accordance with another embodiment of the invention.

As shown in FIG. 9, biosensor 350 includes top and bottom plates 352, 354, which are separated from one another by a spacer 368. Plates 352, 354 are each formed to include a tab 356. Tab 356 includes lateral borders 358, 360 that include a first tapered portion 362 and a second portion 364 extending between tapered portion 362 and an end 366. It is appreciated that the angle of first taper portion 362 as well as the length of second portion 364 can vary in accordance with this disclosure.

Figure 10:
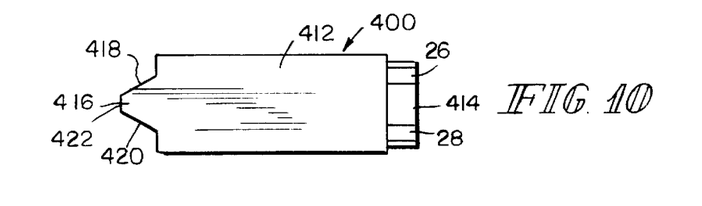
FIG. 10 is a top view of a biosensor in accordance with another embodiment of the invention.

Further, as shown in FIG. 10, biosensor 400 includes top and bottom plates 412, 414, which are separated from one another by a spacer (not shown). Plates 412, 414 are each formed to include a tab 416. Tab 416 includes lateral borders 418, 420 that converge toward end 422. It is appreciated that borders 418, 420 can converge toward one another at a variety of angles in accordance with this disclosure.

FIG. 11 illustrates biosensor 450 in accordance with this invention. Biosensor 450 includes a top plate 452 and a bottom plate (not shown), which are separated from one another by a spacer 456. Each plate has a concave-shaped first end 458 and opposite lateral borders 460, 462. Additionally, ends 458 and a portion 464 of lateral borders 460, 462 define a fluid sample-receiving portion in communication with the capillary space.

Figure 12:
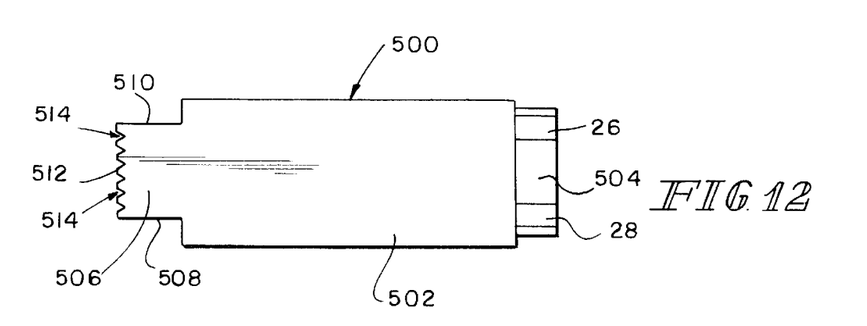
FIG. 12 is a top view of a biosensor in accordance with another embodiment of the invention.

FIG. 12 illustrates biosensor 500 in accordance with this invention. Biosensor 500 includes a top plate 502 and a bottom plate 504, which are separated from one another by a spacer (not shown). Plates 502, 504 are each formed to include a tab 506. Tab 506 includes lateral borders 508, 510, and a free end 512. End 512 includes a plurality of V-shaped notches 514 therein. It is appreciated end 512 can include any number of notches formed in a variety of shapes and sizes in accordance with this disclosure.

Figure 13:
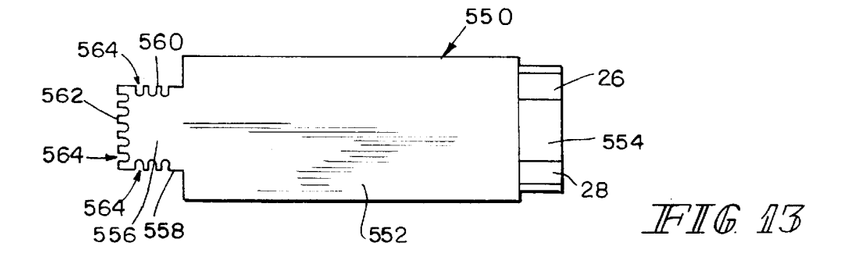
FIG. 13 is a top view of a biosensor in accordance with another embodiment of the invention.

FIG. 13 illustrates biosensor 550 in accordance with this invention. Biosensor 550 includes a top plate 552 and a bottom plate 554, which are separated from one another by a spacer (not shown). Plates 550, 552 are each formed to include a tab 556. Tab 556 includes lateral borders 558, 560, and a free end 562. Borders 558, 560 and end 562 include a plurality of concave notches 564 therein. It is appreciated borders 558, 560 and end 562 can each include any number of notches formed in a variety of shapes and sizes in accordance with this disclosure.

Although the invention has been described in detail with reference to a preferred embodiment, variations and modifications exist within the scope and spirit of the invention as described and defined in the following claims.

What is claimed is:

1. A biosensor comprising:
    first and second plate elements, said plate elements having first and second ends and first and second lateral borders, the first ends being generally concave in shape,
    a spacer positioned to lie between the first and second plate elements spaced-apart from the first ends so that at least a portion of the first and second plate elements cooperate with one another to form opposite walls of a capillary space and the first ends and at least a portion of the opposite lateral borders define a fluid sample receiving portion in communication with the capillary space, and
    electrodes positioned in the capillary space.

2. The biosensor of claim 1, wherein the lateral borders are straight.

3. The biosensor of claim 2, wherein the lateral borders are parallel relative to one another.

4. The biosensor of claim 1, wherein the lateral borders are curved.

5. The biosensor of claim 1, wherein the spacer is an adhesive.

6. A biosensor comprising:
    first and second plate elements, said plate elements having first and second ends and first and second lateral borders,
    a spacer positioned to lie between the first and second plate elements so that at least a portion of the first and second plate elements cooperate with one another to form opposite walls of a capillary space and the first ends and at least a portion of the opposite lateral borders define a fluid sample receiving portion in communication with the capillary space, and
    electrodes positioned in the capillary space, wherein the ends of the first and second plate elements are off-set from one another.

7. The biosensor of claim 6, wherein the ends of the first and second plate elements are parallel relative to one another.

8. The biosensor of claim 6, wherein the lateral borders are straight.

9. The biosensor of claim 8, wherein the lateral borders are parallel relative to one another.

10. The biosensor of claim 8, wherein the lateral borders converge toward the first ends.

11. The biosensor of claim 6, wherein the lateral borders are curved.

12. The biosensor of claim 6, wherein the spacer is an adhesive.

13. The biosensor of claim 1, wherein at least a portion of the lateral borders are generally concave in shape.

14. A biosensor comprising:
    first and second plate elements, said plate elements each having a body portion with opposite edges and first and second ends extending between the opposite edges and a tab extending from the first end of the body portion, the tab including an end and lateral borders extending between the end of the tab and the first end of the body portion, the lateral borders being spaced-apart from the opposite edges of the body portion,
    electrodes positioned on the tab of said first plate element, and
    a spacer positioned to lie between the plate elements so that the tabs form opposite walls of a capillary space extending between lateral borders and ends, wherein the ends and lateral borders cooperate to define a fluid sample receiving portion in communication with the capillary space.

15. The biosensor of claim 14, wherein the tabs are rectangular in shape.

16. The biosensor of claim 14, wherein the tabs are triangular in shape.

17. The biosensor of claim 14, wherein the tabs are curved.

18. A biosensor comprising:
    first and second plate elements, said plate elements having tabs with ends and first and second lateral borders,
    electrodes positioned on the tab of said first plate element, and
    a spacer positioned to lie between the plate elements so that the tabs form opposite walls of a capillary space extending between lateral borders and ends, wherein the ends and lateral borders cooperate to define a fluid sample receiving portion in communication with the capillary space, wherein the tabs are rectangular in shape and the ends of the first and second plate elements are off-set relative to one another.

19. The biosensor of claim 18, wherein the lateral borders are the same length as the ends.

20. The biosensor of claim 18, wherein the tabs are rectangular in shape.

21. The biosensor of claim 18, wherein the tabs are triangular in shape.

22. The biosensor of claim 18, wherein the tabs are curved.

23. The biosensor of claim 18, wherein the lateral borders converge from the tab end toward the end of the body portion.

24. A biosensor comprising:

first and second plate elements, said plate elements including body portions with edges having a first dimension and opposite ends and tabs extending from one of the opposite ends, the tabs including lateral borders having a second dimension, which is less than the first dimension, the tabs being spaced-apart from the edges of the body portions, electrodes positioned between the tabs, and a spacer positioned to lie between the edges of the body portions so that the tabs form opposite walls of a capillary space, the spacer being spaced-apart from the lateral borders of the tabs and wherein the tabs cooperate to define a fluid sample receiving portion in communication with the capillary space.

25. The biosensor of claim 24, wherein the lateral borders are straight.

26. The biosensor of claim 25, wherein the tabs are rectangular in shape.

27. The biosensor of claim 24, wherein the tabs are triangular in shape.

28. The biosensor of claim 24, wherein the lateral borders are curved.

29. A biosensor comprising:

first and second plate elements, said plate elements including body portions with edges having a first dimension and opposite ends and tabs extending from one of the opposite ends, the tabs including lateral borders having a second dimension, which is less than the first dimension, electrodes positioned between the tabs, and a spacer positioned to lie between the edges of the body portions so that the tabs form opposite walls of a capillary space, wherein the tabs cooperate to define a fluid sample receiving portion in communication with the capillary space, wherein the lateral borders are straight and the tabs include ends and the ends of the tab have a third dimension that is equal to the second dimension.

* * * * *